United States Patent [19]

Suzuki

[11] 4,404,192

[45] Sep. 13, 1983

[54] PROCESS FOR PREPARING COMPOSITIONS FOR PERFUSING ARTIFICIAL KIDNEY SYSTEMS FOR DIALYSIS

[75] Inventor: Takeshi Suzuki, Itano, Japan

[73] Assignee: Tomita Pharmaceutical Corporation, Limited, Tokushima, Japan

[21] Appl. No.: 253,931

[22] PCT Filed: Aug. 20, 1980

[86] PCT No.: PCT/JP80/00186

§ 371 Date: Apr. 27, 1981

§ 102(e) Date: Apr. 14, 1981

[87] PCT Pub. No.: WO81/00515

PCT Pub. Date: Mar. 5, 1981

[30] Foreign Application Priority Data

Aug. 27, 1979 [JP] Japan ............................... 54-109365

[51] Int. Cl.³ ...................... A61K 33/06; A61K 33/14
[52] U.S. Cl. ..................................... 424/153; 424/154
[58] Field of Search ................................ 424/153, 154

[56] References Cited

FOREIGN PATENT DOCUMENTS 51-51511 5/1976 Japan.

*Primary Examiner*—Stanley J. Friedman
*Attorney, Agent, or Firm*—Larson and Taylor

[57] ABSTRACT

A process for preparing a composition having low hygroscopicity, in the form of uniform particles and useful for perfusing artificial kidney systems from compounds to give an electrolyte ion composition comprising $Na^+$, $K^+$, $Ca^{++}$, $Mg^{++}$, $Cl^-$ and $CH_3COO^-$ ions in specified proportions, the process being characterized by dissolving the compounds in warm water, allowing the solution to stand for at least 6 hours and thereafter spray-drying the resulting aqueous solution of mixed salts by spraying the solution into a drying chamber having an inlet temperature of 200° to 400° C. from the orifice of a pressurized nozzle having an orifice diameter of 1.0 to 2.0 mm.

2 Claims, No Drawings

PROCESS FOR PREPARING COMPOSITIONS FOR PERFUSING ARTIFICIAL KIDNEY SYSTEMS FOR DIALYSIS

TECHNICAL FIELD

This invention relates to a process for preparing compositions for perfusing artificial kidney systems for dialysis, and more particularly to a process for preparing a novel composition which is useful for perfusing artificial kidney systems for dialysis and which has very low hygroscopicity, is in the form of uniform particles and can be reconstituted to a specified composition of electrolyte ions with ease and stability at all times.

BACKGROUND ART

Conventionally dialysates (hemodialysates) having the following electrolyte ion composition are solely used for perfusing artificial kidney systems for dialysis although the composition may differ slightly in accordance with the symptoms of the patient, the type of the dialyzer, etc.

| | |
|---|---|
| $Na^+$ | 126–145 mEq/ml |
| $K^+$ | 1.5–3.0 mEq/ml |
| $Ca^{++}$ | 2.5–4.0 mEq/ml |
| $Mg^{++}$ | 1.0–1.5 mEq/ml |
| $Cl^-$ | 98–108 mEq/ml |
| $CH_3COO^-$ | 30–42.5 mEq/ml |
| Glucose | 0–300 mg/dl |
| Total osmotic pressure | 260–317.9 mO sm |

In view of solubility, such known dialysate is prepared as a concentrate having a volume of about 10 liters and the corresponding weight relative to about 3 kg of the requisite electrolyte ions in theoretical weight and is diluted to 350 liters for use, so that the actual use of the dialysate involves the serious problems that the concentrate itself requires a space and is inconvenient to transport. Further because of the problems, such as the space required, the whole 10-liter quantity of the dialysate is usually enclosed in a plastics container as a commercial product, while the electrolyte ion composition of the product differs from lot to lot. Additionally it has been realized in recent years that the commercial product undergoes variations in pH with time and is unable to retain the ion composition as prepared. Thus it has been desired in the industry concerned to develop a perfusate which is uniform in quality and easy to preserve and handle. To reduce the volume and weight, it appears useful to prepare a mixture of particulate inorganic or organic salts in conformity with the composition of electrolyte ions for affording a dialysate. In fact, a perfusate has been proposed which is prepared by physically mixing salts together with use of a particle forming machine of the wet type or dry type. However, for the preparation of this product, the salts used as the component compounds are merely mixed together physically in specified proportions. The dialysate must contain the electrolyte ions accurately in the specified proportions. For example, potassium chloride must be incorporated in the specified amount of as small as 0.01 to 0.03 times the amount by weight of sodium chloride. Difficulties are therefore encountered in preparing a mixture batchwise by accurately weighing out small quantities of the components and mixing them together. When the mixture is produced in large batches, it is extremely difficult to uniformly mix the components which differ in specific gravity, so that when a required quantity of the resulting mixture is diluted with water for use, the dialysate obtained contains greatly altered proportions of the electrolyte ions. Thus the mixture has the fatal defect that it can not be reconstituted actually with the prescribed ion proportions. Moreover, the ingredients to be mixed together are all highly hygroscopic and have the drawback that even when allowed to stand in air in the form of a mixture, they adsorb water and become sticky or agglomerate. Such moisture retaining product is likely to deteriorate, while it is difficult to accurately weigh out required quantities for use. Furthermore the proposed particulate product is inherently uneven in particle size, is prone to agglomeration to form secondary particles as mentioned above and is therefore of very low commercial value in appearance. The product has another disadvantage that it requires a cumbersome procedure for reconstitution with water since the ingredients have different solubilities.

An object of the present invention is to provide a process for preparing with good reproducibility a perfusing composition which retains a specified quality at all times and which can be preserved and handled satisfactorily.

Another object of the invention is to provide a process for preparing a particulate mixture of salts which is useful for dialysis with artificial kidney systems and which is uniform in particle size, has very low hygroscopicity and can be easily reconstituted to a dialysate having a homogenenous composition of electrolyte ions.

Another object of the invention is to provide a process for preparing a particulate mixture of salts which is useful for dialysis with artificial kidney systems and which has none of such drawbacks that the known dialysates require a substantial space, are inconvenient to transport, alter in quality when preserved for a prolonged period of time and vary from lot to lot in electrolyte ion composition.

DISCLOSURE OF THE INVENTION

The present invention relates to a process for preparing a composition having low hygroscopicity, in the form of uniform particles and useful for perfusing artificial kidney systems from compounds to give an electrolyte ion composition comprising $Na^+$, $K^+$, $Ca^{30+}$, $Mg^{++}$, $Cl^-$ and $CH_3COO^-$ ions in specified proportions, the process being characterized by dissolving the compounds in warm water, allowing the solution to stand for at least 6 hours and thereafter spray-drying the resulting aqueous solution of mixed salts by spraying the solution into a drying chamber having an inlet temperature of 200° to 400° C. from the orifice of a pressurized spray nozzle having an orifice diameter of 1.0 to 2.0 mm.

The present invention has been accomplished based on the following findings. Our research revealed that when known dialysates for artificial kidney systems were spray-dried, it was impossible to obtain uniform particles as desired, while an aqueous solution of mixed salts separately prepared to give the same electrolyte ion composition as the above-mentioned dialysate, even if spray-dried, was unable to afford the desired particles. If possible, the resulting powder was inferior in respect of solubility and hygroscopicity, or it was difficult to reconstitute the powder to a dialysate having the specified electrolyte ion composition, or the dialysate obtained involved variations in ion composition. Thus difficulties were encountered in preparing uniform particles with good reproducibility. However, during the research subsequently conducted, we have incidentally found that when a solution of the ingredient compounds in warm water is allowed to stand for at least 6 hours after dissolving and thereafter spray-dried under specific conditions, uniform particles can be obtained always with outstanding reproducibility and desired excellent characteristics but free of any of the foregoing drawbacks.

The process of this invention affords a particulate mixture of salts with good stability and exceedingly high reproducibility at all times. The mixture has ingredients incorporated therein in specified proportions, is uniform in particle size, has very low hygroscopicity and can be easily reconstituted to a dialysate having a homogeneous composition of electrolyte ions. The mixture obtained by the process of the invention are in the form of particles resembling minute balls of uniform size and each having the specified composition. Accordingly the present mixture distinctly differs from the particulate mixtures produced by a particle forming machine in that the mixture can be reconstituted, with stability and ease at all times, to a dialysate having a definite electrolyte ion composition. The mixture has substantially no hygroscopicity and is preservable for a prolonged period of time without entailing deterioration. Moreover the particulate mixture of salts according to the invention has none of the drawbacks of conventional dialysates that they require a substantial space, are inconvenient to transport, alter in quality when preserved for a long period of time and vary from lot to lot in electrolyte ion composition. Merely when a required quantity of the mixture weighed out is diluted with water or with water containing glucose which is usually used for the adjustment of osmotic pressure, the resulting composition is very advantageously usable as a dialysate which always has proper ion proportions, for an artificial kidney dialyzer equipped with a centralized supply means and serviceable for many patients or for a dialyzer for individual use or of compact type.

According to the present invention, the ingredient compounds are dissolved in warm water to prepare an aqueous solution of mixed salts having the same electrolyte ion composition as the dialysate for artificial kidney systems. Preferably the proportions of the ions in the composition are in the following ranges.

| | |
|---|---|
| $Na^+$ | 126–145 mEq/l |
| $K^+$ | 1.5–3.0 mEq/l |
| $Ca^{++}$ | 2.5–4.0 mEq/l |
| $Mg^{++}$ | 1.0–1.5 mEq/l |
| $Cl^-$ | 98–108 mEq/l |
| $CH_3COO^-$ | 30–42.5 mEq/l |

Examples of useful ingredient compounds for preparing the ion composition are sodium chloride, potassium chloride, calcium chloride, magnesium chloride and sodium acetate. Such compounds may be those containing bound water (crystal water), e.g. $CaCl_2.2H_2O$, $MgCl_2.6H_2O$, etc. It is critical that these compounds be dissolved in warm water having a temperature preferably of about 35° to 40° C. The aqueous solution of mixed salts obtained must be allowed to stand at room temperature for at least 6 hours, preferably for about 6 to 12 hours, after dissolving. When cold water is used, or when the solution is spray-dried immediately after preparation, it is difficult to obtain uniform particles as desired. The powder then obtained is uneven in composition as well as in particle size, with difficulty encountered in reconstituting the powder to a dialysate having a specified electrolyte ion composition. The aqueous solution of mixed salts is prepared more advantageously by placing the salts into warm water at about 35° to 40° C. and stirring the mixture. Preferably the aqueous solution of the ingredients has the highest possible concentration. It is suitable that the solution have a concentration usually of about 35%.

After the aqueous solution of mixed salts has been allowed to stand at room temperature for at least 6 hours, the solution is spray-dried under specific conditions according to the invention. For spray drying, the aqueous solution is forced out from the orifice of a nozzle at an increased pressure and thereby atomized. The drying temperature condition for this procedure somewhat varies with the diameter of the orifice used, the concentration of the aqueous solution, etc. Usually the solution is introduced into the drying chamber at an inlet temperature of about 200° to 400° C., preferably about 350° to 400° C. This corresponds to the outlet temperature of the drying chamber of about 100° to 200° C., preferably about 150° to 200° C. The term drying temperature as hereinafter used refers to the inlet temperature of the drying chamber. If the drying temperature is outside the above range, it is difficult to obtain uniform particles as contemplated. Further the orifice diameter of the nozzle used for the spray drying, as well as the drying temperature and the method of preparing the aqueous solution of mixed salt ingredients, significantly influences the shape and properties of the particles obtained. When it is in the range of about 1.0 to 2.0 mm, the desired particulate product can be prepared which is in the form of uniform minute spherical particles, has substantially no hygroscopicity, high solubility and specified composition and can be reconstituted to a homogeneous electrolyte ion composition with good stability and ease at all times. When the nozzle used has an orifice diameter other than is specified above, it is impossible to obtain a powder having such outstanding characteristics. The pumping pressure for feeding the solution for the spray drying can be determined suitably, the standard pressure being 10 kg/cm² generally. The solution can be dried to the desired particulate mixture of inorganic salts usually within a very short period of time, i.e. several seconds to several tens of seconds. The particulate product thus obtained is composed of uniform minute spherical particles usually in the range of about 100 to 500μ.

The present invention will be described below in greater detail with reference to the following examples.

EXAMPLE 1

Quantities of the following ingredients are accurately weighed out in the specified proportions by weight and are dissolved in warm water (40° C.) within a stirring tank with stirring to prepare an aqueous solution having a high concentration of about 35%.

| | | |
|---|---|---|
| Sodium chloride (as NaCl) | 64.442 | wt. % |
| Potassium chloride (as KCl) | 1.660 | " |
| Calcium chloride (as $CaCl_2.2H_2O$) | 2.047 | " |
| Magnesium chloride (as $MgCl_2.6H_2O$) | 1.698 | " |
| Sodium acetate (as $CH_3COONa$) | 30.152 | " |

Twelve hours after the concentrated aqueous solution has been prepared as above, the solution is sprayed into a continuous spray-drying apparatus (inlet temperature 360°–380° C., outlet temperature 160°–180° C.) from a nozzle having an orifice diameter of 2.0 mm, with the application of pressure, i.e. at a pumping pressure of 10 kg/cm$^2$, whereby a particulate mixture of inorganic salts (fine particles) is obtained according to the invention.

Twenty-gram portions are randomly collected from the powder as specimens Nos. I to V and diluted with same quantities of water individually to obtain dialysate specimens. The electrolyte ion composition of these specimens are quantitatively determined, using a flame spectrophotometer for Na$^+$ and K$^+$ ions, the EDTA titration method for Ca$^{++}$ and Mg$^{++}$ ions, the perchloric acid (0.1 NHClO$_4$) titration method for CH$_3$COO$^-$ ion and the argentometric titration method for Cl$^-$ ion. Table 1 below shows the results.

TABLE 1

| Specimen No. | Na$^+$ | K$^+$ | Ca$^{++}$ | Mg$^{++}$ | Cl$^-$ | CH$_3$COO$^-$ | Total ions in dilution |
|---|---|---|---|---|---|---|---|
| (Theoretical value) | 132 | 2 | 2.5 | 1.5 | 105 | 33 | 276 mEq/l |
| I | 132.0 | 2.0 | 2.5 | 1.5 | 105.2 | 32.8 | 276.0 |
| II | 131.9 | 2.0 | 2.5 | 1.5 | 105.1 | 32.8 | 275.8 |
| III | 132.2 | 1.9 | 2.5 | 1.5 | 105.4 | 32.7 | 276.2 |
| IV | 132.0 | 2.0 | 2.5 | 1.5 | 105.2 | 32.7 | 275.9 |
| V | 132.0 | 2.0 | 2.5 | 1.5 | 105.2 | 32.8 | 276.0 |
| Average value (X) | 132.0 | 1.98 | 2.5 | 1.5 | 105.22 | 32.76 | 275.96 |

Table 1 reveals that each of the five specimens prepared according to the invention and randomly selected can be reconstituted to a dialysate having a uniform electrolyte ion composition.

Next, the particulate mixture of inorganic salts of the invention obtained in Example 1 is checked for changes with the lapse of time. The powder is allowed to stand at room temperature for 6 months. Portions of specified quantity are weighed out immediately after preparation and 1 month, 3 months and 6 months after preparation.

Each of the portions is dissolved in water (containing 0.1 to 0.2%/liter of glucose) for reconstitution to obtain 1.0 liter of dialysate (total osmotic pressure: about 280 mO sm). Table 2 below shows the pH of the dialysate and the percent content of each component thereof based on the corresponding content determined immediately after preparation as 100.

TABLE 2

| | Dissolved on preparation | Dissolved in 1 month | Dissolved in 3 months | Dissolved in 6 months |
|---|---|---|---|---|
| NaCl | 100 | 100.05 | 100.05 | 100.05 |
| KCl | 100 | 100.88 | 100.88 | 100.15 |
| CaCl$_2$ | 100 | 99.16 | 100.36 | 99.76 |
| MgCl$_2$ | 100 | 100.79 | 99.35 | 99.35 |
| CH$_3$COONa | 100 | 99.23 | 98.90 | 98.99 |
| Glucose | 100 | 99.90 | 100.13 | 100.1 |
| pH | 7.32 | 7.33 | 7.32 | 7.32 |

Table 2 above shows that the powder prepared according to the invention remains very stable despite the lapse of time and can be reconstituted to a dialysate even after preservation for a long period of time without entailing any substantial changes as compared with the dialysate prepared immediately after production.

COMPARISON EXAMPLE 1

The same quantities of the same ingredients as used in Example 1 are mixed together in a particle forming machine to obtain a particulate mixture of inorganic salts.

In the same manner as in Example 1, 20-gram portions of the powder are weighed out and similarly diluted with water to prepare dialysate specimens. The ion composition of each specimen is quantitatively determined. Table 3 below shows the results.

TABLE 3

| Specimen No. | Na$^+$ | K$^+$ | Ca$^{++}$ | Mg$^{++}$ | Cl$^-$ | CH$_3$COO$^-$ | Total ions in dilution (mEq/l) |
|---|---|---|---|---|---|---|---|
| (Theoretical value) | 132 | 2 | 2.5 | 1.5 | 105 | 33 | 276 |
| I | 131.3 | 2.1 | 2.4 | 1.6 | 104.6 | 32.8 | 274.8 |
| II | 131.3 | 2.2 | 2.3 | 1.7 | 104.8 | 32.7 | 275 |
| III | 131.9 | 2.1 | 2.3 | 1.6 | 104.1 | 33.8 | 275.8 |
| IV | 131.5 | 2.0 | 2.6 | 1.5 | 104.6 | 33.3 | 275.5 |
| V | 131.1 | 1.9 | 2.5 | 1.5 | 103.5 | 33.5 | 274.0 |
| Average value (X) | 131.42 | 2.06 | 2.42 | 1.58 | 104.32 | 33.22 | 275.02 |

Table 3 above reveals that when the five specimens randomly collected from the same lot prepared by mixing are diluted with water even under the same conditions, the specimen dilutions vary considerably in electrolyte ion composition. A comparison between Table 3 and Table 1 indicates that the process of the invention affords particles of very high quality.

COMPARISON EXAMPLE 2

The same quantities of the same ingredients as used in Example 1 are weighed out and then dissolved in water (containing 350 to 700 g of glucose) to obtain 10 liters of concentrated solution (having a total osmotic pressure of about 280 mO sm when diluted with water 35-fold to a dialysate) corresponding to commercial dialysate concentrates. The resulting dialysate is preserved in a 10-liter plastics container.

The dialysate thus obtained is diluted and thereafter tested in the same manner as in Example 1 for changes due to the lapse of time. Table 4 below shows the results.

TABLE 4

|  | On preparation | In 1 month | In 3 months | In 6 months |
|---|---|---|---|---|
| NaCl | 100 | 99.39 | 97.11 | 96.94 |
| KCl | 100 | 99.41 | 97.20 | 95.73 |
| $CaCl_2$ | 100 | 97.97 | 94.38 | 92.59 |
| $MgCl_2$ | 100 | 98.63 | 95.03 | 92.87 |
| $CH_3COONa$ | 100 | 98.73 | 97.12 | 96.76 |
| Glucose | 100 | 99.41 | 98.37 | 98.10 |
| pH | 7.20 | 7.32 | 7.40 | 7.37 |

The results listed in Table 4 above, as compared with Table 2, indicate that the commercial dialysate alters in composition and pH with time, fails to retain the initial electrolyte ion composition after long-term preservation and therefore involves problems for actual use, whereas the powder obtained by the invention is usable free of such variations despite the lapse of time and is very useful.

INDUSTRIAL APPLICABILITY

As described above, the process of the present invention affords perfusing compositions which retain a specified quality at all times and which can be preserved and handled satisfactorily. The compositions are well suited as dialysates for use in artificial kidney dialyzers.

I claim:

1. A process for preparing a composition having low hygroscopicity, in the form of uniform particles and useful for perfusing artificial kidney systems from compounds to give an electrolyte ion composition comprising 126–145 mEq/l of $Na^+$, 1.5—3.0 mEq/l of $K^+$, 2.5–4.0 mEq/l of $Ca^{++}$, 1.0–1.5 mEq/l of $Mg^{++}$, 98–108 mEq/l of $Cl^-$ and 30–4.52 mEq/l of $CH_3COO^-$, said process comprising dissolving the compounds in warm water having a temperature of about 35° to 40° C., allowing the solution to stand for at least 6 hours, and thereafter spray-drying the resulting aqueous solution of mixed salts by spraying the solution into a drying chamber having an inlet temperature of 200° to 400° C. from the orifice of a spray nozzle having an orifice diameter of 1.0 to 2.0 mm to form said composition.

2. A process as claimed in claim 1 wherein the aqueous solution of mixed salts has a concentration of about 35%.

* * * * *